United States Patent
Kottu

(10) Patent No.: US 12,000,724 B2
(45) Date of Patent: Jun. 4, 2024

(54) CONTROLLED LIQUID DOSE DISPENSER

(71) Applicant: Jagadeesh Sreenivas Kottu, Hyderabad (IN)

(72) Inventor: Jagadeesh Sreenivas Kottu, Hyderabad (IN)

(*) Notice: Subject to any disclaimer, the term of this patent is extended or adjusted under 35 U.S.C. 154(b) by 531 days.

(21) Appl. No.: 17/270,880

(22) PCT Filed: Nov. 19, 2018

(86) PCT No.: PCT/IB2018/059104
§ 371 (c)(1),
(2) Date: Feb. 24, 2021

(87) PCT Pub. No.: WO2020/044104
PCT Pub. Date: Mar. 5, 2020

(65) Prior Publication Data
US 2021/0190566 A1 Jun. 24, 2021

(30) Foreign Application Priority Data
Aug. 25, 2018 (IN) .............................. 201841031905

(51) Int. Cl.
*G01F 11/02* (2006.01)
*A61C 19/06* (2006.01)
*A61M 31/00* (2006.01)
*B05B 11/00* (2023.01)

(52) U.S. Cl.
CPC .......... *G01F 11/025* (2013.01); *A61C 19/063* (2013.01); *A61M 31/00* (2013.01); *B05B 11/0035* (2013.01); *A61M 2210/0618* (2013.01); *A61M 2210/0625* (2013.01); *A61M 2210/0662* (2013.01)

(58) Field of Classification Search
CPC ................ B43K 23/008; G01F 11/025; A45D 2200/055
USPC .................................................. 401/172, 262
See application file for complete search history.

(56) References Cited

U.S. PATENT DOCUMENTS

| | | | | |
|---|---|---|---|---|
| 4,624,594 A * | 11/1986 | Sasaki | ...................... | G01F 11/08 401/172 |
| 4,752,015 A * | 6/1988 | Schumacher | ...... | B65D 47/2018 401/262 |
| 4,838,722 A * | 6/1989 | Katz | ..................... | B05C 17/005 401/101 |
| 7,314,327 B2 * | 1/2008 | Byun | ................. | B65D 83/0016 401/172 |
| 8,745,825 B2 * | 6/2014 | Gitman | .................. | B25G 1/102 16/430 |
| 9,156,601 B2 | 10/2015 | Tani | | |

* cited by examiner

*Primary Examiner* — David P Angwin
*Assistant Examiner* — Bradley S Oliver
(74) *Attorney, Agent, or Firm* — Jose Cherson Weissbrot

(57) ABSTRACT

According to an aspect of the present invention, a liquid dose dispenser 100 is disclosed. The dispenser 100 comprises a main body having a front assembly 138, a mid assembly 148 and a rear assembly 140. The dispenser 100 comprises a reservoir (liquid container) 134, a liquid dispensing tip 136, a lead screw 130 for guiding the screw in the mid assembly 148. It also comprises a cam 126, a nut 128, and a spring element 132 wherein the spring element retracts the lead screw for controlled dispensing of the liquid. The said dispenser is used for dispensing required doses of liquids, solutions, viscous fluids for pharmaceutical, nutraceutical and food applications.

2 Claims, 11 Drawing Sheets

CONTROLLED LIQUID DOSE DISPENSER

FIELD OF THE INVENTION

Embodiments of the present invention relate to a controlled liquid dose dispenser for dispensing liquids. Specifically, the present invention relates to a controlled liquid dose dispenser in the shape of a pen for dispensing liquids in specified quantities accurately.

BACKGROUND OF THE INVENTION

Precise dispensing of liquids is useful in food and pharmaceutical industry to distribute small quantities of solutions, chemicals, reagents, medicines, drugs, enzymes, additives etc. In various processes, it is desired to deliver small quantities of valuable reagents necessary to initiate chemical reactions and to get intended results.

Micro-volume liquid handling technologies have been extensively used in the field of molecular biology and have been under rapid development over the last several decades. Accompanying the trend of laboratory automation and high-throughput, the liquid dispensing is increasingly playing.

Dispensing liquid volumes of less than 1 milliliter accurately and reproducibly in a single drop is a long-sought goal in areas as diverse as chemical screening for drug discovery, pharmaceutical formulation, agricultural chemistry, cosmetic and food processing, and ink-jet printing.

Thus, there is a need to develop a dispenser for controlled delivery of liquids which is portable, effective and economical.

SUMMARY OF THE INVENTION

The following is a brief summary of subject matter that is described in greater detail herein. This summary is not intended to be limiting as to the scope of the claims.

It is an object of the invention to provide a controlled liquid dose dispenser for dispensing small amounts of liquids/semi liquids/gels/solutions/viscous liquids accurately.

It is another object of the invention to provide a controlled liquid dose dispenser in the shape of a pen that is easy to carry and to dispense the liquid in a hygienic manner at the desired location.

It is yet another object of the invention to provide a controlled liquid dose dispenser wherein the cap of the pen shaped controlled liquid dose dispenser is used for delivering the liquid from the reservoir present in the pen.

According to an aspect of the present invention, a liquid dose dispenser is disclosed. The dispenser comprises main body having a front assembly, mid assembly and a rear assembly.

In accordance with an aspect of the present invention, the dispenser comprises a reservoir (liquid container), liquid dispensing tip, and textured grip on the outer casing of the front assembly.

In accordance with an aspect of the present invention, the dispenser comprises a lead screw having a lead screw head at a front end, a rubber gasket for guiding the screw in a mid assembly.

In accordance with an aspect of the present invention, the dispenser comprises a stopper at the end of the front assembly for holding the reservoir in contact.

In accordance with an aspect of the present invention, the dispenser comprises a cam, nut, and a spring element present in the mid assembly.

In accordance with an aspect of the present invention, the spring aids in retraction of the structure to the normal position. The dispenser further comprises a slider, an end cap with a female part (groove) and the lead screw extending to the rear end.

In accordance with an aspect of the present invention, the rear assembly controls the dispensing of liquid from the dispenser.

In accordance with an aspect of the present invention, the end cap is a closer of the main body at the rear end with a cap assembly with engaging structure.

In accordance with an aspect of the present invention, the said dispenser is used for dispensing required doses of liquids, solutions, viscous fluids for pharmaceutical, nutraceutical and food applications.

In accordance with an aspect of the present invention, the said dispenser is in the shape of a pen with the cap assembly adapted to be used as a covering to the tip from which the fluid is dispensed.

In accordance with an aspect of the present invention, the said cap assembly comprises an engaging structure from inside.

In accordance with an aspect of the present invention, the said engaging structure present in the cap fit to the female part (groove) in the end cap.

In accordance with an aspect of the present invention, the said structures present in the cap activate the valve of the dispensing system.

In accordance with an aspect of the present invention, the said the engaging structure present in the cap pushes the female part in the end cap.

In accordance with an aspect of the present invention, the said cap assembly is detachable from the pen shaped dispenser body.

In accordance with an aspect of the present invention, the said dispenser comprises a non-return valve (not shown), for allowing liquid from the reservoir.

In accordance with an aspect of the present invention, the said lead screw acts as a plunger assembly having a plunger element and a liquid-tight seal and the plunger assembly is extending from the reservoir.

In accordance with an aspect of the present invention, the said dispenser is used for dispensing controlled amount of liquid/medicine in nose, ears, mouth or onto the other parts of the body. The medicine in the dose range of 0.01 ml to 2 ml is delivered accurately.

In accordance with an aspect of the present invention, the said dispenser is used in dental applications for dispensing medicine in the form of fluid or semi fluid to teeth or in between tooth.

In accordance with an aspect of the present invention, the said dispenser is used for dispensing required amount of dosage of fluid accurately in upward, sideward or in any intended direction.

In accordance with an aspect of the present invention, the said dispenser is used for dispensing enzymes in a food industry.

In accordance with an aspect of the present invention, the said dispenser is used for dispensing required amount of dosage of fluid accurately in upward, sideward or in any intended direction.

In accordance with an aspect of the present invention, the said dispenser is a disposable type dispenser.

BRIEF DESCRIPTION OF THE DRAWINGS

Example embodiments of the present invention are illustrated by accompanying drawings, wherein.

DETAILED DESCRIPTION OF THE INVENTION

Figures 1A, 1B:
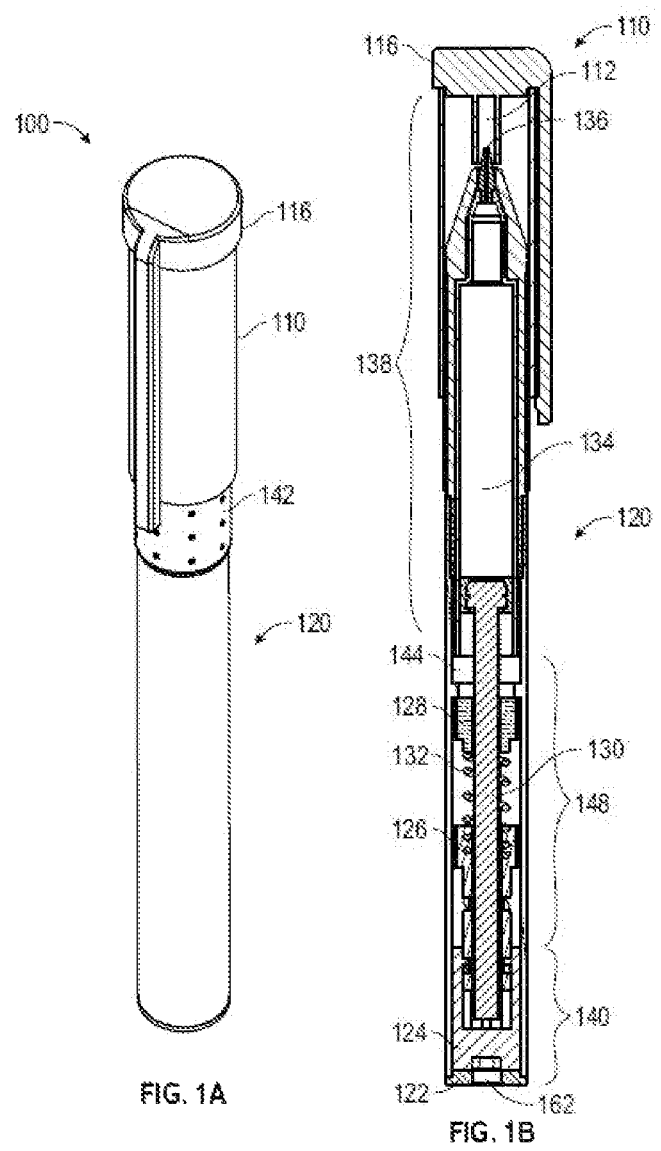
FIG. 1A illustrates perspective of view and FIG. 1B illustrates side sectional view of the controlled liquid dose dispenser according to an embodiment of the invention.

A controlled liquid dose dispenser in the shape of pen is disclosed. The following description is merely exemplary in nature and is not intended to limit the present invention, applications, or uses. Throughout the drawings, corresponding reference numerals indicate like or corresponding parts and features.

FIG. 1A illustrates perspective view and FIG. 1B illustrates front sectional view of the controlled liquid dose dispenser according to an embodiment of the invention. As shown in FIGS. 1A and 1B, the controlled liquid dose dispenser 100 is present in the shape of a pen. The controlled liquid dose dispenser 100 has a cap 110 with engaging structure 112, main body assembly 120, an end cap 122, cam engaging slider 124, cam 126, nut 128, lead screw 130, spring 132, reservoir (liquid container) 134, liquid dispensing tip 136, front end assembly 138, rear assembly 140, grip 142, stopper 144, lead screw 130, lead screw head 152. The cap 110 is present at the front side of the controlled liquid dose dispenser 100 when the controlled liquid dose dispenser 100 is not dispensing liquid. The cap 122 is detachable from the main body assembly 120.

Figure 2:
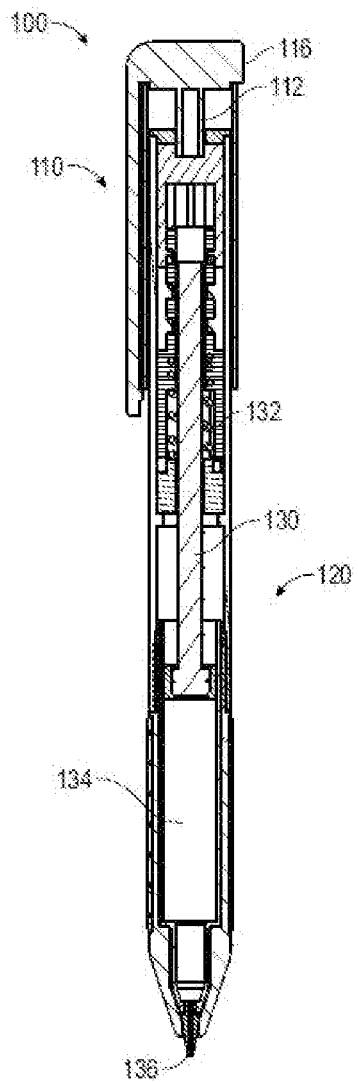
FIG. 2 illustrates perspective view of controlled liquid dose dispenser with cap inserted from back of the pen shaped dispenser according to an embodiment of the invention.

FIG. 2 illustrates a front view of controlled liquid dose dispenser 100 with cap 110 inserted from back of the main body assembly 120 according to an embodiment of the invention. As shown in shown in FIG. 2, the cap 110 is inserted from the rear end 140 of the main body. The cap 110 contains an engaging structure 112 inside of it. When the cap 110 is inserted from the rear side of the main end of the main body assembly 120, the engaging structure 112 acts as a male part and fits into the female part 162 of the end cap 122.

After the fit is attained, the cap 110 is clicked manually on cap head 116 which engages the injector linearly forward that results in the dispensing of liquid in the reservoir 134 through the tip 136. Further the required dosage can be dispensed by the user either based on the number of clicks or as per dosage required.

In one embodiment, the dosage dispensed is about 0.01 ml to 2 ml. The liquid reservoir 134 can store about 2 to 15 ml of the liquid. Once the liquid in the liquid reservoir 134 is over, the user may dispose the controlled liquid dose dispenser 100.

Figure 3A:
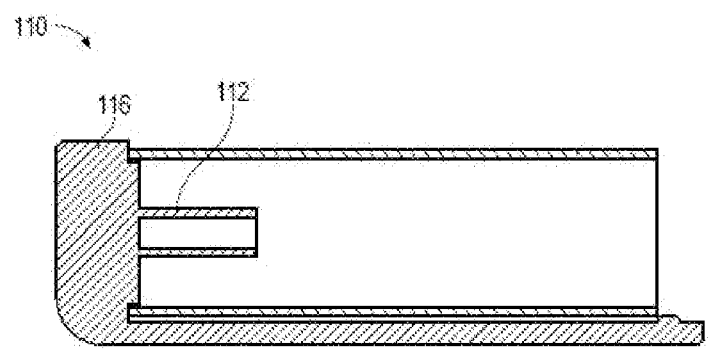
FIG. 3A illustrates side sectional view and FIG. 3B illustrates bottom view of the cap arrangement of controlled liquid dose dispenser according to an embodiment of the invention.
Figure 3B:
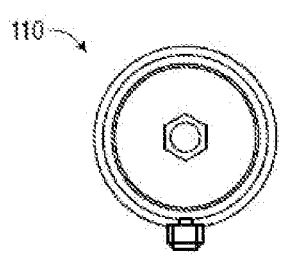

FIGS. 3A and 3B illustrate the cross-sectional view of the controlled liquid dose dispenser cap arrangement 110 and bottom view of the cap arrangement 110 respectively. The cap 110 is present at the front side of the liquid dose dispenser 100.

As shown in FIG. 3A, the cap 110 is detachable from the pen shaped liquid dose dispenser 100 body and is inserted from rear end 140 of the main body that contains engaging structure 112 inside (not shown in FIGS. 3A and 3B).

The engaging structure 112 will be inserted in to the female portion 162 provided at the end cap 122 of the liquid dispenser.

In one embodiment of the invention, the operation of the dispenser is carried out only when the cap 110 is inserted at the back of the rear side of the main end of the main body and cap head 116 is operated manually by click mechanisms.

Figure 4A:
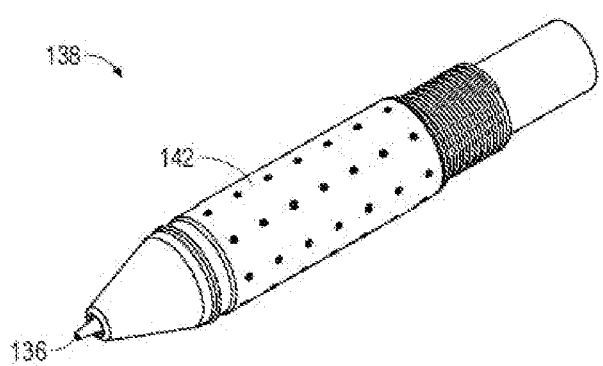
FIG. 4A illustrates perspective view.
Figure 4B:
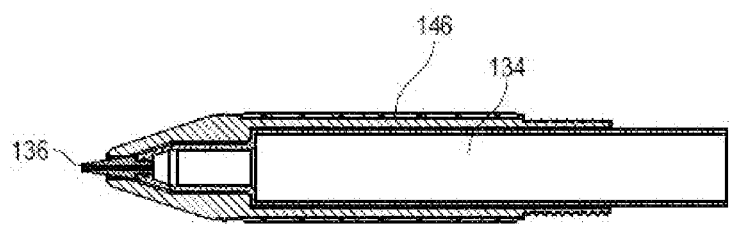
FIG. 4B illustrates side sectional view and FIG. 4C illustrates bottom view of the front assembly of controlled liquid dose dispenser according to an embodiment of the invention.
Figure 4C:
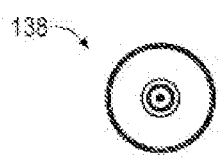

FIG. 4A illustrates front assembly 438 of controlled liquid dose dispenser perspective view, FIG. 4B illustrates front view and FIG. 4C illustrates side view of front assembly 138 of liquid dose dispenser.

The front assembly 138 of pen shaped controlled liquid dose dispenser 100 includes a reservoir (liquid container) 134, liquid dispensing tip 136 and grip 142.

The reservoir 134 is present in the main body 100. The reservoir 134 stores the liquid to be dispensed. The lead screw 130 pushes the liquid towards the tip 136 during dispensing of the liquid. The liquid container (reservoir) 434 stores about 2 ml to 15 ml of the liquid that is used for dispensing the liquid as per the requirement.

The tip 136 of the controlled liquid dispenser is generally made of polypropylene and is integrated with the front assembly 138. The dosage is dispensed from the tip 136 in the specified amounts by the user.

When the cap 110 is inserted at the rear assembly 140 of the pen shaped liquid dispenser 100, the lead screw 130 pushes the liquid present in the reservoir 134 towards the tip 1360 by clicking the head cap 116 as many times as the dosage required.

In one embodiment of the present invention, the dosage dispensed is in the range of 0.01 ml to 2 ml.

The outer shell 146 of the main body can be transparent so that the volume of the liquid present in the reservoir 134 can be viewed from outside without opening the main body.

In one embodiment of the invention the outer body of the main body is opaque so that it can remain unexposed to the surroundings.

Figure 5A:
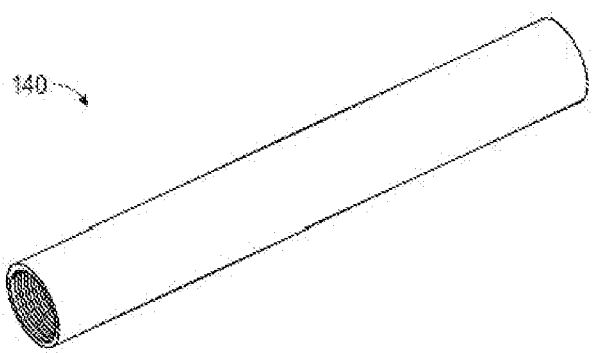
FIG. 5A illustrates perspective view.
Figure 5B:
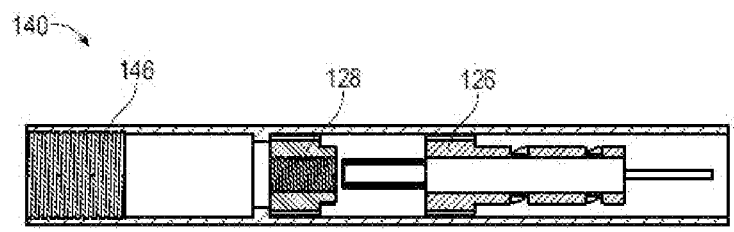
FIG. 5B illustrates side sectional view and FIG. 5C illustrates top view of the mid assembly of controlled liquid dose dispenser according to an embodiment of the invention.
Figure 5C:
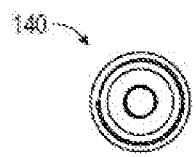

FIG. 5 illustrates rear assembly 140 of controlled liquid dose dispenser according to an embodiment of the invention. FIG. 5A displays a hollow cylindrical shape with internal thread grip 146 at front end, FIG. 5B displays front view of the rear assembly 140. The rear assembly comprises of nut 128, cam 126 and cam engaging slider 124 and a lead screw 130. The rear assembly 140 is an arrangement of controlled liquid dose dispenser according to an embodiment of the invention. As shown in FIG. 5B, the outer shell of the dispensing system is made of polymers like ABS, PU, and HDPE etc. It protects the all internal parts according to an embodiment of the invention.

Figure 6A:
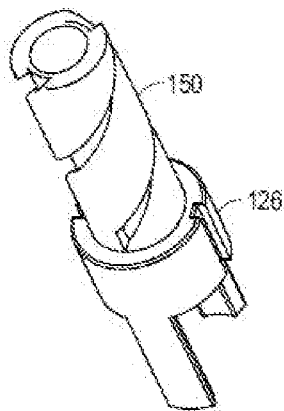
FIG. 6A illustrates perspective view.
Figure 6B:
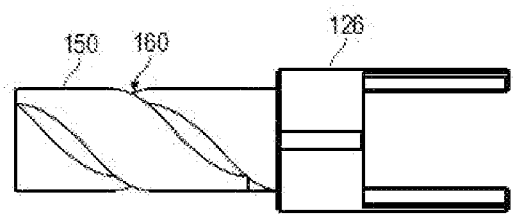
FIG. 6B illustrates side sectional view.
Figure 6C:
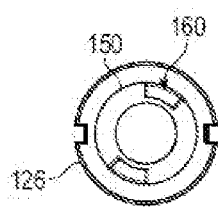
FIG. 6C illustrates top view and FIG. 6D illustrates bottom views of the cam assembly of controlled liquid dose dispenser according to an embodiment of the invention.
Figure 6D:
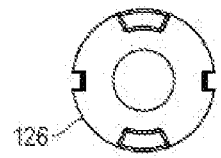

FIG. 6A illustrates the perspective view and FIG. 6B illustrates front view and FIGS. 6C and 6D illustrate corresponding side views of the cam assembly 126 of controlled liquid dose dispenser according to an embodiment of the invention. As shown in FIG. 6B the linear movement of the lead screw 130 is guided by the cam 126 that engages the lead screw 130 to serve the purpose of liquid dispensing. The slider 150 moves the cam 126. The slider 150 has two projections one at each end (not shown in FIGS. 6A and 6B). The movement of the cam 126 in forward direction helps in pushing the lead screw 130 which in turn pushes the liquid inside the reservoir 134 through the tip 136 for the desired dosage of the liquid dose dispenser.

Figure 7A:
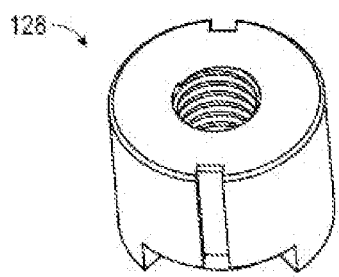
FIG. 7A illustrates perspective view.
Figure 7B:
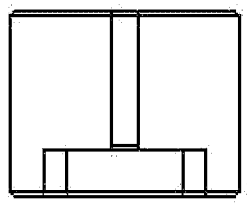
FIGS. 7B, 7C illustrate the side sectional views.
Figure 7C:
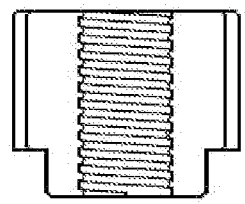
Figure 7D:
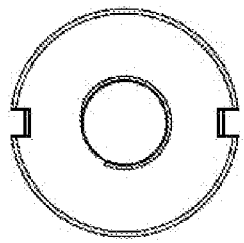
FIG. 7D illustrates top view and FIG. 7E illustrates bottom of a nut assembly of controlled liquid dose dispenser according to an embodiment of the invention.
Figure 7E:
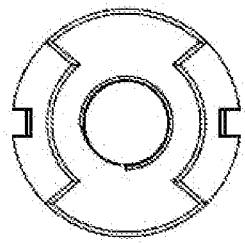

FIG. 7A illustrates perspective view, FIGS. 7B, 7C illustrate the side sectional views, FIG. 7D illustrates top view and FIG. 7E illustrates bottom of a nut assembly of controlled liquid dose dispenser according to an embodiment of the invention. As shown in FIGS. 7A to 7D, the nut assembly 128 rotates and the lead screw 130 which connects to the reservoir (liquid container) 134 moves forward.

Figure 8A:
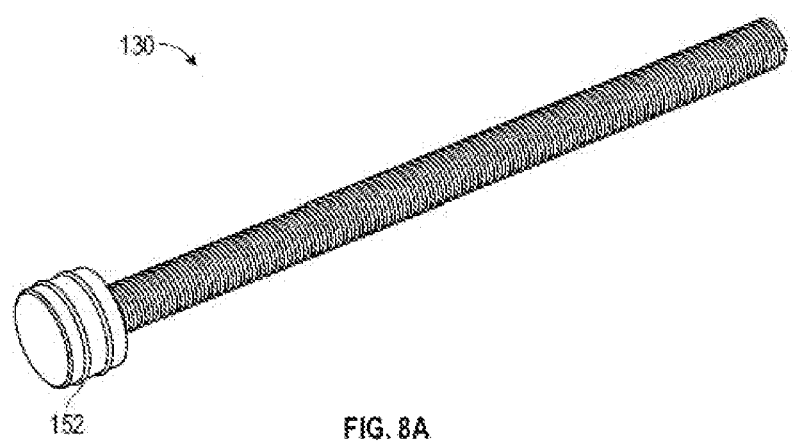
FIG. 8A illustrates perspective view.
Figure 8B:
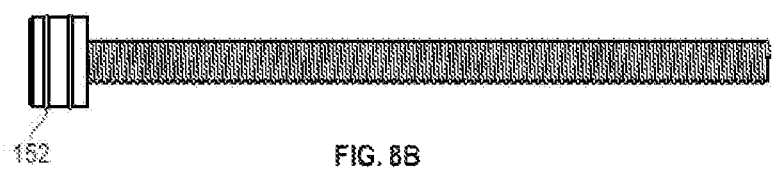
FIG. 8B illustrates side sectional view.
Figure 8C:
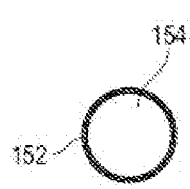
FIGS. 8C and 8D illustrate top and bottom views of the injector assembly of controlled liquid dose dispenser according to an embodiment of the invention.
Figure 8D:
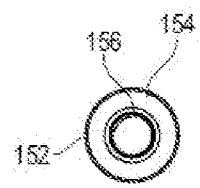

FIG. 8A illustrates perspective view, FIG. 8B illustrates side sectional view, FIGS. 8C and 8D illustrate top and bottom views of the injector assembly of controlled liquid dose dispenser according to an embodiment of the invention. As shown in FIG. 8A to 8D, the lead screw 130 has an inner face having a rubber gasket 152 towards the liquid reservoir 134 and an outer face for engaging a lead screw 130 that may be manually operated using the pen cap slider mechanism. During the operation of the controlled liquid dose dispenser, the lead screw pushes the liquid reservoir 134 in the forward direction for dispensing of the liquid.

Figure 9A:
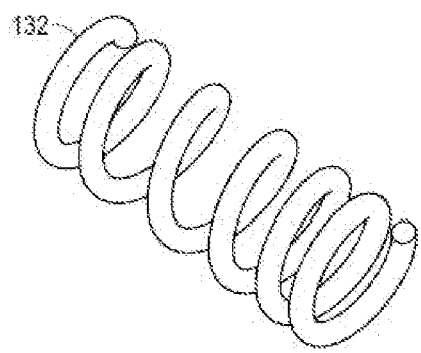
FIG. 9A illustrates perspective view.
Figure 9B:
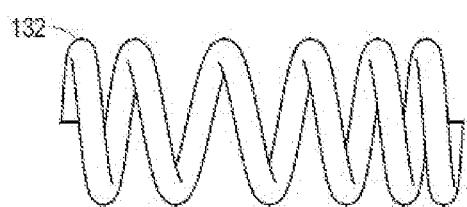
FIG. 9B illustrates side sectional view and FIG. 9C illustrates bottom view of the coil assembly of controlled liquid dose dispenser according to an embodiment of the invention.
Figure 9C:
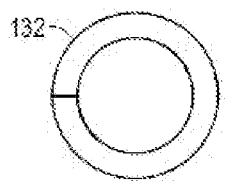

FIG. 9A illustrates perspective view and FIG. 9B illustrates side sectional view and FIG. 9C illustrates bottom view of the coil assembly of controlled liquid dose dispenser according to an embodiment of the invention. As shown in FIGS. 9A to 9C, the coil 132 is mounted on the lead screw 130, to serve the clicking mechanism that is used for dispensing the required dosage. The coil 932 helps in retraction of the cam assembly (not shown in FIGS. 9A to 9C) after dispensing of the liquid.

Figure 10A:
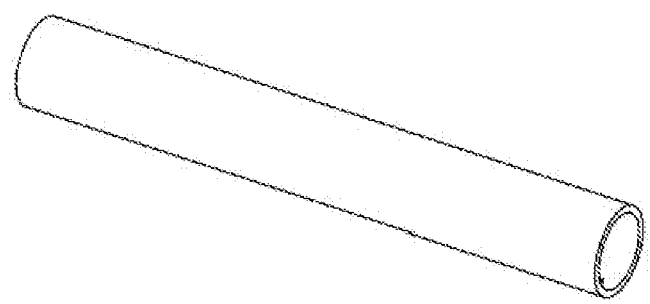
FIG. 10A illustrates perspective view.
Figure 10B:
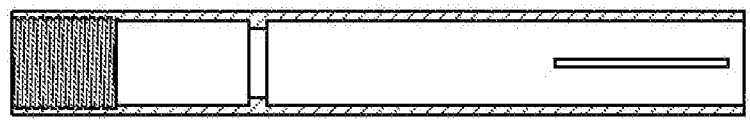
FIG. 10B illustrates side sectional view and FIG. 10C illustrates bottom of the mid shell assembly of controlled liquid dose dispenser according to an embodiment of the invention.
Figure 10C:
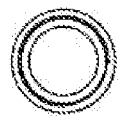

FIG. 10A illustrates perspective view, FIG. 10B illustrates side sectional view and FIG. 10C illustrates bottom of the mid shell assembly of controlled liquid dose dispenser according to an embodiment of the invention. As shown in FIGS. 10A to 10C, the mid shell acts as a casing for the entire mid body that covers all the interior parts like lead screw 130, nut 128, cam 126 and end cap 122. The mid shell 148 is therein attached to the front assembly 138 of the liquid dose dispenser.

Figure 11A:
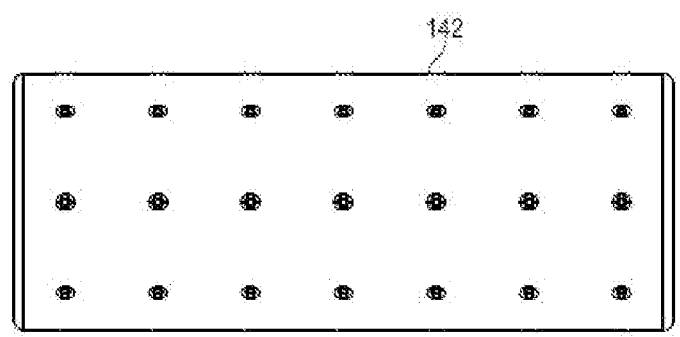
FIG. 11A illustrates perspective view and FIG. 11B illustrates bottom view of grip of the controlled liquid dose dispenser according to an embodiment of the invention.
Figure 11B:
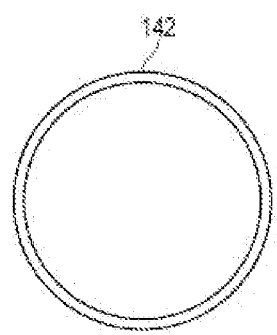

FIG. 11A illustrates perspective view and FIG. 11B illustrates bottom view of grip of the controlled liquid dose dispenser according to an embodiment of the invention. As shown in FIGS. 11A and 11B, the grip 142 helps the user to hold the main body assembly (not shown in FIGS. 11A and 11B) firmly so that a comfortable hold is assured.

I claim:

1. A liquid dose dispenser (100), comprises:
    a cap assembly (110) having a cap head (116) and an outer wall extending from the cap head, the cap head (116) including an engaging structure (112) protruding from the cap head (116) and radially inward of the outer wall, wherein the cap assembly (110) enables a non-working position and a working position of the liquid dose dispenser 100 based on the engaging structure; and
    a main body assembly (120) having a front assembly (138), a mid assembly (148), and a rear assembly (140); wherein the cap assembly (110) is detachably attachable to the main body assembly (120) along the front assembly (138) in the non-working position, and detachably attachable to the main body assembly (120) along the rear assembly (140) in the working position, the main body further having:
        a reservoir (134) in the front assembly (138) to store liquid to be dispensed,
        a liquid dispensing tip (136) in a front of the front assembly (138) to dispense the liquid stored in the reservoir,
        an outer covering around the liquid dispensing tip (136) to cover the liquid dispensing tip (136),
        a textured grip (142) on an outer casing of the front assembly (138),
        a lead screw (130) having a lead screw head (154) at a front end, and a rubber gasket (152) at the lead screw head (154) for guiding the screw in the mid assembly (148) of the dispenser (100) to push the liquid towards the liquid dispensing tip (136) for dispensing of the liquid from the reservoir, wherein the lead screw (130) extends in the front assembly (138), the mid assembly (148), and the rear assembly (140),
        a stopper 144 at an end of the front assembly (138) of the main body for holding the reservoir intact, wherein the lead screw head (154) of the lead screw (130) rests on a first face of the stopper (144),
        a cam (126), a nut (128), and a spring element (132) present in the mid assembly (148), and engaged with the lead screw (130) such that the spring element (132) lies between the cam (126) and the nut (128) to aid retraction of the lead screw (130) to the non-working position, wherein the nut (128) rests on a second face, opposite to the first face, of the stopper (144),
        a cam engaging slider (124) in the rear assembly (140) and engages with a rear end of the lead screw (130), wherein the cam engaging slider (124) also engages with the cam (126),
        an end cap (122) with a female part (162) at a rear end of the rear assembly (140), wherein the rear assembly (140) controls the dispensing of liquid from the dispenser (100), and the end cap is a closer of the main body at the rear end with the cap assembly (110) with engaging structure (112),
    wherein the cap assembly (110), in the non-working position, is attachable with the front assembly (138), whereby the liquid is not dispensed from the reservoir, and
    wherein the cap assembly (110), is in the working position, the cap assembly (110) is attachable to the end cap (122), whereby the engaging structure (112) of the cap assembly (122) fits to the female part (162) in the end cap (122) so that the outer wall of the cap assembly (110) lies radially outward of the body of the liquid dose dispenser (100), and when the cap assembly (110) is clicked manually, the cam engaging slider 124 moves in a forward direction, thereby moving the cam (126) in the forward direction that presses the spring element (132) and rotates the nut assembly, in-turn pushing the lead screw (130) in the forward direction which in-turn pushes the liquid inside the reservoir (134) to dispense therefrom, and wherein the liquid dose dispenser is used for dispensing required doses of liquids, solutions, viscous fluids for pharmaceutical, nutraceutical and food applications.

2. The liquid dose dispenser of claim 1 comprising a shape of a pen with the cap assembly (110) adapted to be used as a covering to the liquid dispensing tip (136) from which the fluid is to be dispensed.

\* \* \* \* \*